(12) United States Patent
Roe

(10) Patent No.: US 6,410,821 B1
(45) Date of Patent: Jun. 25, 2002

(54) DIRECTIONALLY PREFERENTIAL WASTE PASSAGE MEMBER FOR USE WITH DISPOSABLE ABSORBENT ARTICLE

(75) Inventor: Donald C. Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/669,079

(22) Filed: Sep. 25, 2000

Related U.S. Application Data

(63) Continuation of application No. 09/106,423, filed on Jun. 29, 1998, now Pat. No. 6,160,200.

(51) Int. Cl.$^7$ ................................................ A61F 13/15
(52) U.S. Cl. .................. 604/378; 604/364; 604/385.01
(58) Field of Search ................................ 604/364, 368, 604/385.08, 385.01, 378

(56) References Cited

U.S. PATENT DOCUMENTS

| | | | | |
|---|---|---|---|---|
| 3,563,241 A | | 2/1971 | Evans ........................ 128/284 |
| 4,009,313 A | * | 2/1977 | Crawford et al. ........... 428/290 |
| 4,643,726 A | | 2/1987 | Gegelys ...................... 604/368 |
| 4,793,337 A | * | 12/1988 | Freeman et al. ............. 128/156 |
| 5,062,840 A | | 11/1991 | Holt et al. ............... 604/385.19 |
| 5,176,672 A | | 1/1993 | Bruemmer et al. ...... 604/385.1 |
| 5,260,345 A | | 11/1993 | Desmarais et al. .......... 521/148 |
| 5,397,316 A | | 3/1995 | LaVon et al. ................ 604/369 |
| 5,425,726 A | | 6/1995 | Shimizu et al. ........... 604/385.1 |
| 5,462,541 A | | 10/1995 | Bruemmer et al. .......... 604/391 |
| 5,763,044 A | | 6/1998 | Ahr et al. .................... 428/131 |
| 5,830,201 A | | 11/1998 | George et al. ............... 604/364 |

FOREIGN PATENT DOCUMENTS

| | | | | |
|---|---|---|---|---|
| EP | 0 626 160 | 11/1994 | ........... A61F/13/15 |
| EP | 0 661 031 | 7/1995 | ........... A61F/13/15 |
| EP | 0 815 819 | 1/1998 | ........... A61F/13/15 |
| JP | 2-31756 | 2/1990 | ........... A61F/13/15 |
| JP | 10-28702 | 2/1998 | ........... A61F/13/54 |
| JP | 10-192342 | 7/1998 | ........... A61F/13/54 |
| WO | WO 98/16180 | 4/1998 | ........... A61F/13/15 |
| WO | WO 98/29461 | 7/1998 | ............. C08F/8/32 |
| WO | WO 98/29501 | 7/1998 | ............. C08L/1/28 |
| WO | WO 98/29502 | 7/1998 | ........... C08L/23/02 |
| WO | WO 98/29506 | 7/1998 | ........... C08L/29/04 |
| WO | WO 98/29508 | 7/1998 | ........... C08L/51/06 |
| WO | WO 98/29517 | 7/1998 | .......... C09J/129/10 |
| WO | WO 98/29585 | 7/1998 | ............. D01F/8/00 |
| WO | WO 98/29590 | 7/1998 | ............. D04H/1/00 |

* cited by examiner

*Primary Examiner*—John G. Weiss
*Assistant Examiner*—C. Lynne Anderson
(74) *Attorney, Agent, or Firm*—Michael P. Hayden; David M. Weirich; Ken K. Patel

(57) ABSTRACT

The present invention provides an absorbent article having a first waist region, an opposed second waist region, a crotch region disposed between the first waist region and the second waist region. The absorbent article preferably comprises a liquid impervious backsheet material, an absorbent core and a directionally preferential waste passage member. The waste passage member has a body facing surface and an opposed garment facing surface, at least a portion of the body facing surface of the waste passage member including a soluble material capable of dissolving when contacted by bodily exudates so as to permit the bodily exudates to pass through the waste passage member in a direction generally away from the wearer's skin. At least a portion of the garment facing surface of the waste passage member includes a barrier material which resists penetration by the bodily exudates in a direction opposite from the first direction. The waste activated barrier member is preferably disposed in at least a portion of the crotch region of the absorbent article.

6 Claims, 4 Drawing Sheets

DIRECTIONALLY PREFERENTIAL WASTE PASSAGE MEMBER FOR USE WITH DISPOSABLE ABSORBENT ARTICLE

This application is a continuation of application Ser. No. 09/106,423, filed on Jun. 29, 1998 now U.S. Pat. No. 6,160,200.

FIELD OF THE INVENTION

The present invention relates to a directionally preferential waste passage member which can be used separately or in conjunction with absorbent articles such as diapers, adult incontinence products, sanitary napkins and the like, to reduce skin contamination by wastes discharged from the body. More particularly, the invention relates to disposable absorbent articles including one or more waste passage members which permit bodily exudates to pass through the member(s) in one direction, but which restrict the movement of the exudates through the member(s) in the reverse direction.

BACKGROUND OF THE INVENTION

The major function of absorbent articles such as diapers and adult incontinence briefs is to prevent body exudates from soiling, wetting, or otherwise contaminating clothing or other articles, such as bedding, that may come in contact with the wearer. In recent years, disposable diapers, such as those disclosed in U.S. Pat. No. 5,151,092 issued to Buell et al., have become very popular and have generally replaced durable cloth absorbent articles because of their convenience and reliability. However, despite the effectiveness of such disposable absorbent articles, body exudates often still leak or are stored in the diaper such that the exudates soil and/or irritate the skin of the wearer. Additionally, body exudates often adhere aggressively to skin, increasing the difficulty of cleaning and increasing the likelihood of chronic residual contamination.

The undesirable effects of leakage and/or improper containment, difficult cleanup, and/or residual skin contamination are especially evident with regard to fecal matter deposited in the diaper. Feces contained in the diaper can harm the skin of the wearer over time and feces leaking from the diaper almost invariably presents unpleasant, messy clean-ups. Thus, several attempts have been made to add features to diapers such as barriers, pockets, spacers, transverse barriers and the like to limit the movement of the fecal material across the topsheet and/or to better confine the fecal matter in the diaper. However, such attempts have been generally unsuccessful due to their cost and complexity. Several attempts have also been made to provide topsheets with large apertures through which bodily wastes can pass without resistance. (An example of an aperture in an article applied to the buttocks is disclosed in Japanese Laid Open Patent Application No. HEI 2-31756, filed on Jul. 22, 1988 and published on Feb. 1, 1990.) However, such embodiments are difficult to use because in order to provide any benefit, the caregiver must properly align the aperture with the wearer's anus and/or urethra. This is an especially difficult task when diapering an active child or when fitting a garment to one's self Further, the aperture must somehow be maintained in the proper position throughout the time the diaper is worn in order to be effective.

Accordingly, it would be desirable to provide an element which helps keep feces and other bodily exudates away from the skin of the wearer. Further, it would be advantageous to provide an economical disposable article with the ability to minimize the negative effects of feces or other bodily waste on the wearer or the caregiver. It would also be advantageous to provide an article which can be used in conjunction with an absorbent article which permits bodily exudates to pass in one direction but which resists their passage in the opposite direction. It would also be desirable to provide a barrier sheet which can be used in conjunction with a disposable article which provides an aperture through which bodily exudates can pass where necessary in response to the bodily exudates being expelled from the body. Finally, it would be advantageous to provide such a barrier sheet which is able to be dissolved by bodily exudates moving away from the skin, but resistant to passage of such exudates back toward the skin.

SUMMARY OF THE INVENTION

A disposable article having a first waist region, an opposed second waist region, and a crotch region disposed between the first waist region and the second waist region. The absorbent article preferably comprises: a liquid impervious backsheet material; a directionally preferential waste passage member and an absorbent core disposed between the backsheet and the waste passage member. The waste passage member preferably includes a sheet having a body facing surface and an opposed garment facing surface, at least a portion of the body facing surface of the waste passage member including a soluble material capable of dissolving when contacted by bodily exudates so as to permit the bodily exudates to pass through the waste passage member. At least a portion of the garment facing surface of the waste passage member preferably includes a barrier material which resists penetration by said bodily exudates. The waste passage member is preferably disposed in at least a portion of the crotch region of the absorbent article.

BRIEF DESCRIPTION OF THE DRAWINGS

While the specification concludes with claims particularly pointing out and distinctly claiming the subject matter which is regarded as the: present invention, it is believed that the description will be better understood from the following descriptions which are taken in conjunction with the accompanying drawings in which like designations are used to designate substantially identical elements.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "exudates" and "bodily wastes" are used herein to mean urine, feces, blood, mucous, puss, oils and combinations of these and other substances discharged from the human body. The term "disposable" is used herein to describe absorbent articles which generally are not intended to be laundered or otherwise restored or reused as an absorbent article (i.e., they are intended to be discarded after a single use and, preferably, to be recycled, composted or otherwise discarded in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent and nonabsorbent articles such as incontinence briefs, incontinence undergarments, absorbent inserts, diaper holders and liners, feminine hygiene garments such as tampons, catamenial pads and interlabial devices, wipes, mops, bandages and the like.

Figure 1:
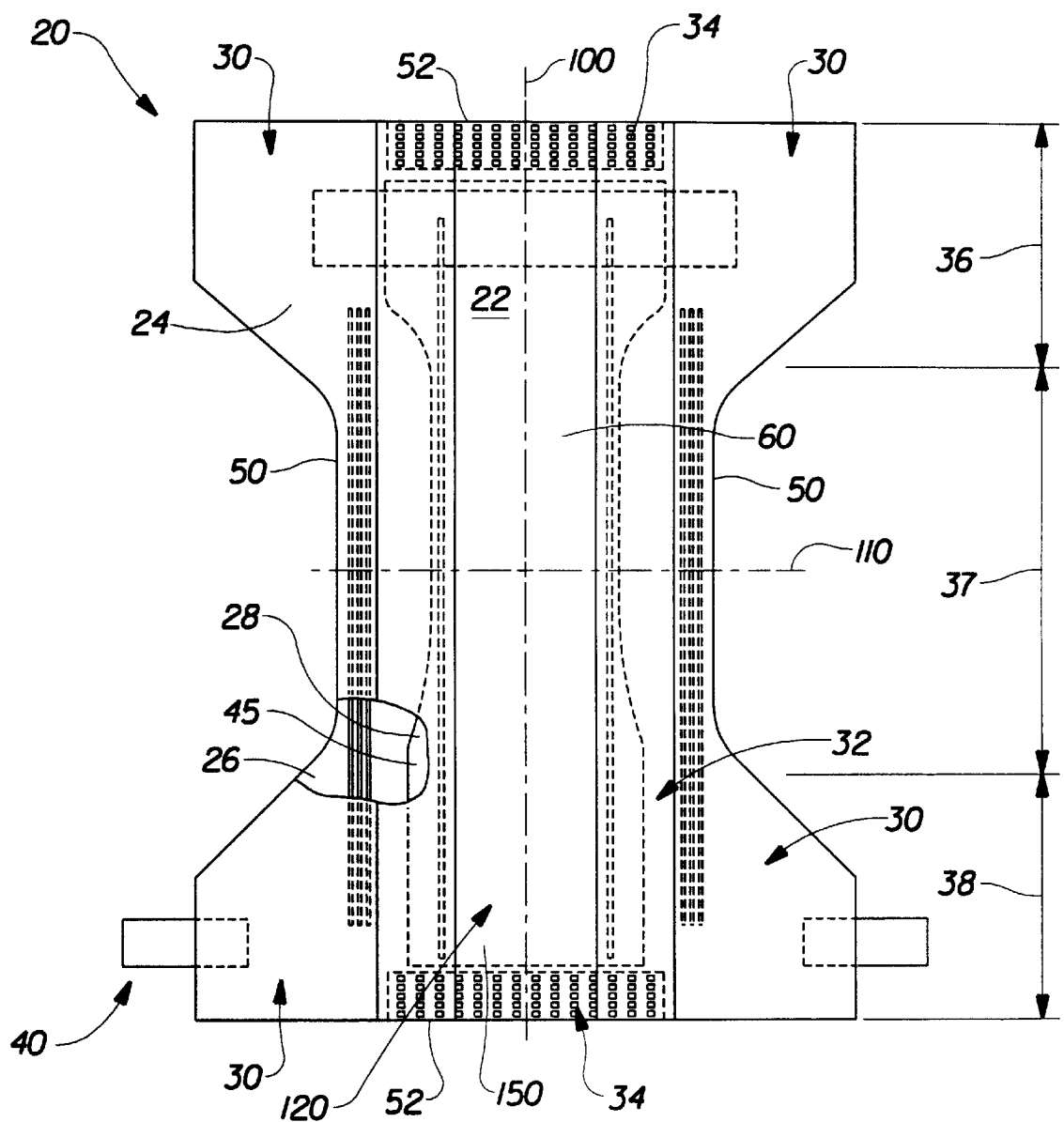
FIG. 1 is a plan view of a diaper including one embodiment of the present invention.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 40. Diaper 20 is shown in FIG. 1 to have a first waist region 36, a second waist region 38 opposed to the first waist region 36 and a crotch region 37 located between the first waist region and the second waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

The backsheet 26 is generally that portion of the diaper 20 positioned adjacent the garment facing surface 45 of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. The SELF web includes a strainable network having at least two contiguous, distinct, and dissimilar regions. Preferably, are of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H. B. Fuller Company of St. Paul, Minn. and marketed as "HL-1620" and "HL-1358-XZP". Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body surface 47 of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet 24 is preferably compliant, soft feeling, and non-irritating to the wearer's skin. Further, at least a portion of the topsheet 24 is liquid pervious, permitting liquids to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the absorbent assemblies include fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the designation "P-8".

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 24 are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein. Alternatively, the topsheet 24 may include an apertured web or film which is hydrophobic. This may be accomplished eliminating the hydrophilizing treatment step from the production process and/or applying a hydrophobic treatment to the topsheet 24, such as a polytetraflouroethylene compound like "SCOTCHGUARD" or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotioned Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The lotion may function alone or in combination with another agent as the hydrophobizing treatment described above. The topsheet 24 may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet 24 or backsheet 26 may be embossed and/or matte finished to provide a more cloth like appearance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20.

Exemplary absorbent structures for use as the absorbent core are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 62 of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also include a fastening system 40. The fastening system 40 preferably maintains the first waist region 36 and the second waist region 38 in an overlapping configuration so as to provide lateral tensions about the circumference of the diaper 20 to hold the diaper 20 on the wearer. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. U.S. Pat. No. 4,662,875 B1 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963,140 issued to Robertson et al. on Oct. 16, 1990. Each of these patents is incorporated herein by reference. In alternative embodiments, opposing sides of the garment may be seamed or welded to form a pant. This allows the article to be used as a pull-on type diaper, such as a training pant.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaperer pulls one elasticized side panel 30 farther than the other during application, the diaper 20 will "self-adjust" during wear.

While the diaper 20 of the present invention preferably has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/155,048 entitled "Absorbent Article With Multi-Directional Extensible Side Panels" filed Nov. 19, 1993 in the names of Robles, et al.; each of which is incorporated herein by reference.

The diaper 20 preferably further includes leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991, and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

In preferred embodiments of the present invention, the absorbent article 20 includes a directionally preferential waste passage member 60 or "waste passage member" 60. The waste passage member 60 is intended to help reduce the amount of feces, urine or other bodily waste discharged by the wearer which comes in contact with or contaminates the skin of the wearer. The reduced contact and skin contamination results from the bodily exudates passing through the waste passage member 60 away from the skin. The waste passage member 60 then acts as a barrier to wastes passing back through its thickness toward the wearer.

Specifically, the waste passage member 60 preferably has a body facing surface 62 and an opposing garment facing surface 64. At least a portion of the body facing surface 62 includes one or more soluble materials 66 which are capable of being dissolved by substances commonly found in human or mammalian bodily waste. Preferably, the waste-soluble substances comprised in the body facing surface 62 are initially capable of providing the structural integrity of the waste passage member 60. Upon excretion, the bodily wastes dissolve a portion of waste passage member 60, thereby eliminating the structural integrity of at least a portion of the waste passage member 60, preferably in the region of the contact between the waste and the waste passage member 60, allowing passage of the waste.

Various properties of the body discharges may trigger or initiate the dissolution of material 66, including but not limited to, moisture, pH, enzymes, temperature, pressure, chemicals (e.g., salts, proteins) and the like. The dissolution of the waste passage member 60 eliminates the structural integrity of at least a portion of the waste passage member 60 in the region of the contact between the waste and the waste passage member 60, allowing the bodily exudates to pass through the waste passage member's thickness in a direction away from the wearer's skin. Further, at least a portion of the garment facing surface 64 of the waste passage member 60 preferably includes a barrier material 70 which resists wetting and/or penetration by the bodily exudates. Thus, once the exudates have passed through the waste passage member 60, they are kept away from the wearer's skin by the resistive properties of the barrier material 70 in at least the portion of the waste passage member 60 not initially dissolved by the waste.

Figure 7:
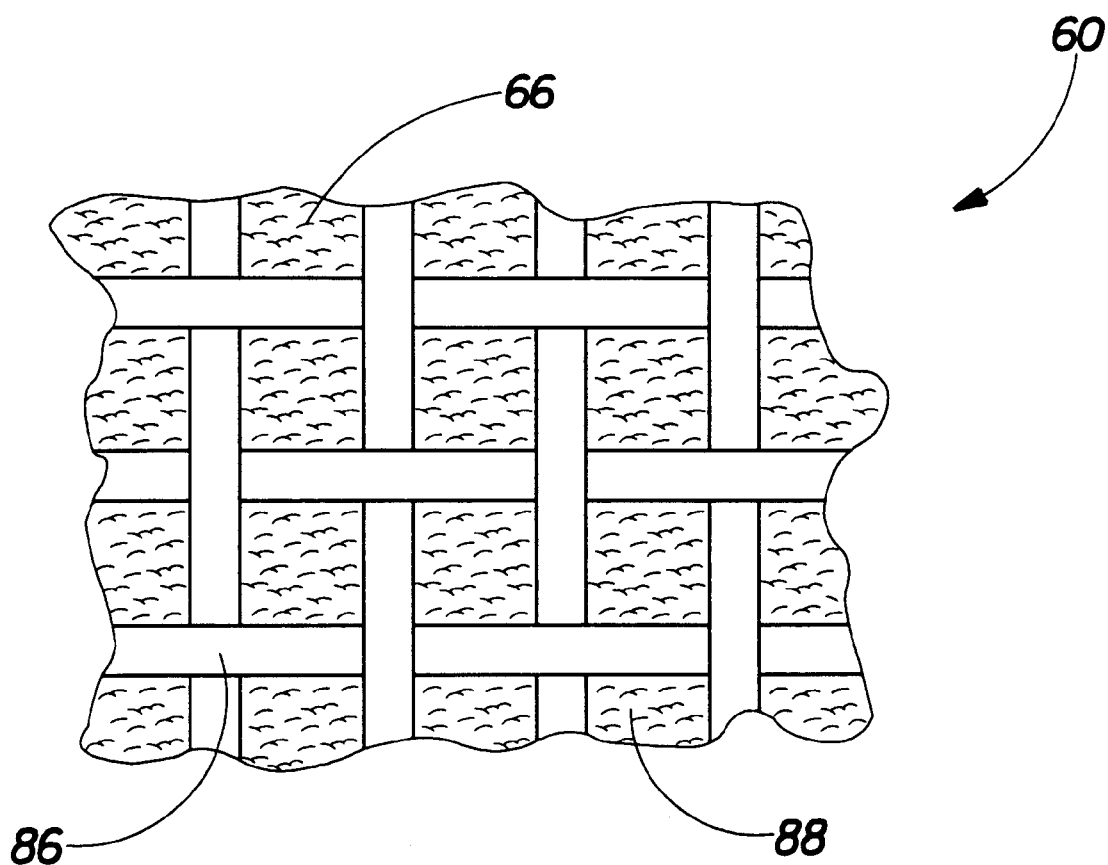
FIG. 7 is a partial, enlarged view of one embodiment of the directionally preferential waste passage member of the present invention.

The waste passage member 60 may comprise any suitable absorbent or nonabsorbent material or materials and may take on any number of configurations. For example, any portion of the waste passage member 60 may include a film, a web, a scrim, a mesh, a foam, a laminate of these or other structures, and the like. In one embodiment, at least a portion of the waste passage member 60 includes only the soluble material 66. In another embodiment, the waste passage member 60 includes insoluble elements such as fibers, filaments or the like, which are held together by the soluble material 66. (As used herein, the term "insoluble" refers to materials which do not dissolve when contacted by the body waste or other material which is intended to dissolve the waste soluble member 66.) In such embodiments, the dissolution of the soluble material 66 permits the structure of waste passage member 60 to disintegrate (i.e. the insoluble elements are no longer held together by the soluble material 66). In yet other embodiments, the waste passage member 60 includes a reticulated insoluble member 86, one example of which is shown in FIG. 7. (As used herein, "reticulated" materials refer to any materials including interstices, apertures, holes or spaces which extend through the thickness of the material in any repeating or non-repeating pattern. The interstices are not limited to any particular size or shape.) The reticulated insoluble member 86 includes interstices 88 or apertures through which bodily waste can pass. In the present invention, at least some of the interstices 88 preferably have a soluble material 66 disposed therein. Thus, when exposed to bodily waste the soluble material 66 disposed in the interstices 88 dissolves and opens the interstices 86 for the passage of the bodily waste. Some or all of the interstices 88 may also include a barrier member 68 so as to prevent bodily wastes from passing through the interstices toward the wearer's skin. Suitable reticulated structures for use with the soluble material 66 include apertured films, scrims, netting, woven and nonwoven webs, foams and the like.

In any embodiment, the soluble material(s) 66 should be readily accessible to exudates deposited on the body facing surface 62 of the waste passage member 60. Suitable water soluble materials include, but are not limited to, polyvinylalcohol, cellulosic materials, starches, polyvinylaniline, polyacrylamide, alginates, water soluble alkyd compositions, and derivatives thereof Some examples of suitable polyvinylalcohol films are available from Hoechst AG, of Frankfurt, Germany, under the trade names "ALCAM" and "AQUAFILM". In preferred embodiments, the film may be between about 0.001 to about 0.5 mm thick and is preferably between about 0.05 and about 0.08 mm thick. However, any portion of the waste passage member 60 may have a different thickness and/or composition so as to provide desired properties including, but not limited to strength, breathability, opacity and rate of dissolution.

The soluble material 66 described above may optionally be pH-sensitive. As used herein, the term "pH sensitive" refers to materials which are insoluble in certain pH ranges, but soluble in others. As such, the soluble material 66 may have a pH threshold. The "pH threshold" of a soluble material is the pH at which the material changes from soluble to insoluble or vice-versa. For example, the soluble material 66 may be substantially insoluble at pH of less than 6, but soluble at a pH of greater than 6. Thus, the pH threshold of that material is a pH of 6. In preferred embodiments, the pH threshold of the soluble material is preferably between about 5 and about 9, and preferably between about 5.5 and about 8.5, although other pH thresholds are contemplated. The change in pH may be the cause or trigger for the dissolution of the soluble material 66, or it may also be used to help increase or decrease the rate of dissolution of the waste passage member 60. Thus, the performance of the waste passage member 60 can be varied depending on factors such as the type and amount of waste deposited onto the article. Exemplary pH-sensitive, soluble materials are known in the art and include but are not limited to, polyacrylamides, phthalate derivatives, formalized gelatin, shellac, keratin, cellulose derivatives (e.g., oxidized cellulose), and polyacrylic acid derivatives. Other preferred pH sensitive, soluble materials include cellulose acetate phthalate, vinyl acetate, polyvinyl acetate phthalate, hydroxypropyl methyl cellulose phthalate, and polymethacrylate blended with acrylic acid and acrylic ester-copolymers. Yet other pH sensitive, soluble materials are described in European Publication EP 612520 A2 entitled "pH Triggered Osmotic Bursting Delivery Devices", the disclosure of which is incorporated by reference herein.

An exemplary pH-sensitive soluble film may be produced by applying onto a surface a thin layer of a solution in acetone of about 4.8 wt % polymethyl methacrylate (PMMA) such as "V920" (available from the Rohm Haas Co., of Philadelphia, Pa.) and 19.0 wt % "EUDRAGIT S-100" (a pH sensitive material available from Creanova, Inc. of Somerset, N.J.), drying the solution until it forms a film and removing the film from the surface. Of course, the ratio of EUDRAGIT S100 to PMMA V920 may be varied, for example, from about 95:5 to about 40:60 or as desired. This film is believed to have a pH threshold of about pH 6.5–7.5 above which the film is water soluble and below which the film is substantially insoluble. An alternative pH sensitive film may be produced using a solution in acetone comprising about 1.8 wt % cellulose acetate such as 398-10 available from Eastman Chemical Co. of Kingsport, Tenn. and about 4.2 wt % cellulose acetate phthalate such as CD-910 available from FMC Corp. of Chicago, Ill. This film is believed to have a pH threshold of about pH 6.0 to about 7.0. As noted above, the ratios of the composition ingredients can be varied as desired, but preferably are between about 95:5 to about 40:60.

The soluble material 66 may also be salt concentration sensitive (e.g., more soluble around either low or high ionic strengths. As such, the soluble material 66 may have a salt concentration (i.e., ionic strength) threshold. The "salt concentration threshold" of a soluble material is the salt concentration at which the material changes from soluble to insoluble or vice-versa. For example, in preferred embodiments the soluble material 66 may be substantially insoluble in distilled water (i.e., salt concentration is essentially zero), but soluble in salt-containing water. Thus, the salt concentration threshold of that material is just above zero. Exemplary materials with this type of salt concentration solubility sensitivity include polyvinyl alcohol materials such as those described in U.S. Pat. Nos. 4,258,849 and 4,245,744, both incorporated herein by reference. Alternatively, the soluble material 66 may be soluble in distilled water, but insoluble in the presence of water containing ions. Exemplary materials with this alternative salt concentration dependence include crown ethers available from Fluka of Buchs, Switzerland as Benzo 15-Crown-5 (catalog no. 12335), Benzo 15-Crown-6 (catalog no. 12338), 15-Crown-5 (catalog no. 28123), and 15-Crown-6 (catalog no. 28125). Preferably, these crown ethers are crosslinked so as to allow the formation of a crystalline-based film. The change in salt concentration may be the cause or trigger for the dissolution of the soluble material 66, or it may also be used to help increase or decrease the rate of dissolution of the waste passage member 60. Thus, the performance of the waste passage member 60 can be varied depending on factors such as the type and amount of waste deposited onto the article.

The soluble material 66 may also be temperature sensitive (e.g., more soluble at either low or high temperatures. As such, the soluble material 66 may have a temperature threshold. The "temperature threshold" of a soluble material is the temperature at which the material changes from insoluble (or a solid) to soluble (or at least partially liquid) or vice-versa. For example, in preferred embodiments the soluble material 66 may be substantially insoluble (i.e., solid) in cold water (e.g., below 35 degrees C.), but soluble (i.e., at least partially liquid) in warmer water. Thus, the temperature threshold of that material is 35 degrees C. Exemplary materials experiencing a transition from solid to liquid with increasing temperature include waxes, gelatin, and pectins. Alternatively, the soluble material 66 may be soluble in cold water, but insoluble at warmer temperatures. Exemplary materials with this alternative temperature dependence include NIPAM (n-isopropylacrylamide), available from Jarchem Industries of Newark, N.J. The change in temperature may be the cause or trigger for the dissolution of the soluble material 66, or it may also be used to help increase or decrease the rate of dissolution of the waste passage member 60. Thus, the performance of the waste passage member 60 can be varied depending on factors such as the type and amount of waste deposited onto the article.

Figure 5:
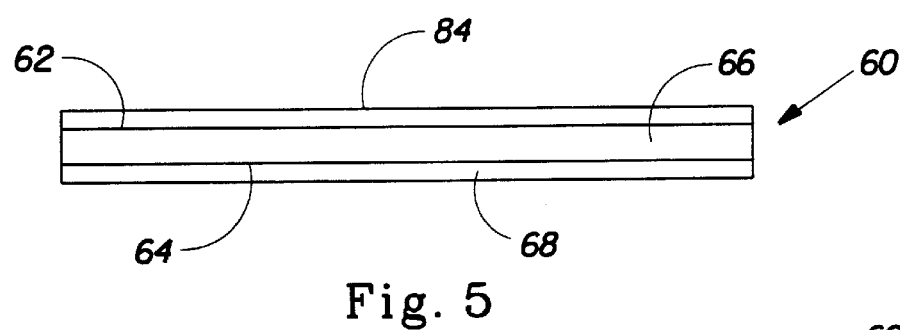
FIG. 5 is a cross sectional view of an alternative embodiment of a directionally preferential waste passage member.

In an alternative embodiment, the dissolution of soluble material 66 may be triggered by enzyme activity. For example, an enzyme present in the article may effect a pH change in conjunction with hydrolysis of bodily waste which in turn promotes dissolution of the soluble member 66 (e.g., a mixture of urease and urea liberates ammonia, resulting in a pH increase). Alternatively, as shown in FIG. 5, a hydrolysis substrate 84 capable of being hydrolyzed by fecal enzymes may be disposed on or adjacent to the body-facing surface 62 of the waste passage member 60. When fecal enzymes hydrolyze the hydrolysis substrate 84, a pH change results which may trigger the dissolution of the soluble material 66. Suitable hydrolysis substrates include keratin, collagen, starch, and triglycerides, urea, and other known substrates for enzymes commonly found in feces. Enzymes found in bodily waste which may effect a pH change in the waste or when contacted with a hydrolysis substrate 84 disposed on the waste passage member 60 include, but are not limited to, proteases, lipases, ureases and the like. In other embodiments, enzyme activity may. effect other chemical or mechanical changes in any portion of the waste passage member 60 such that the waste passage member 60 may permit the passage of bodily waste. In any case, the pH change resulting from the enzyme activity may not only trigger dissolution, but may also help increase or decrease the rate of dissolution of the waste passage member 60.

In yet another embodiment, the waste passage member 60 may comprise an enzyme degradable material 82 which provides structural integrity for the waste passage member 60 until hydrolyzed by an enzyme present in the bodily waste. For example, at least a portion of the waste passage member 60 may comprise a collagen film or binder (or other proteinaceous material) which provides the structural integrity of the waste passage member 60. When hydrolyzed by proteases found in the feces, such as trypsin, chymotrypsin, and the like, the structure of the enzyme degradable member 82 loses its integrity and thus permits the passage of bodily wastes in at least a direction away from the wearer's skin.

At least a portion of the garment facing surface 64 of waste passage member 60 preferably also includes a barrier material 68. As noted above, the barrier material 68 is intended to prevent the bodily wastes which have passed through the waste passage member 60 from moving back through the waste passage member 60 and contaminating the wearer's skin. Thus, the barrier material 68 may include any material or materials which resist, repel or completely block passage of the bodily wastes toward the wearer's skin. The barrier material(s) 68 may be disposed over all or any portion of the garment surface 64 of the waste passage member 60. Further, the barrier material(s) 68 may be incorporated into the waste passage member 60 or may be separately added to any other portion of the waste passage member 60. Some nonlimiting examples of barrier materials include silicone oils or waxes, polytetraflouroethylene coatings, petroleum based waxes and oils such as petrolatum, silicone polymers, and the like. Such barrier materials may be provided by any known means in the form of liquid, solid, or semi-solid oils, waxes, powders, fibers and the like, or any other structures or substances capable of delivering the barrier properties. Examples of suitable barrier materials include silicone oils which are available from Dow Corning, Midland, Mich., under any trade designations #200, #749, and #1401 and Dow Corning silicone waxes such as #2503. Additional suitable barrier materials include any of the skin care compositions or ingredients thereof, described below. The coating level of such silicone oils has been found to be suitable in the range of 0.001 to 1 g/cm$^2$. For example, a #1401 Dow Corning oil may be applied to a surface of a PVA film at an add-on level of 0.06 g/cm$^2$, and subsequently allowed to air dry for 3 days to form a suitable barrier.

Figure 6:
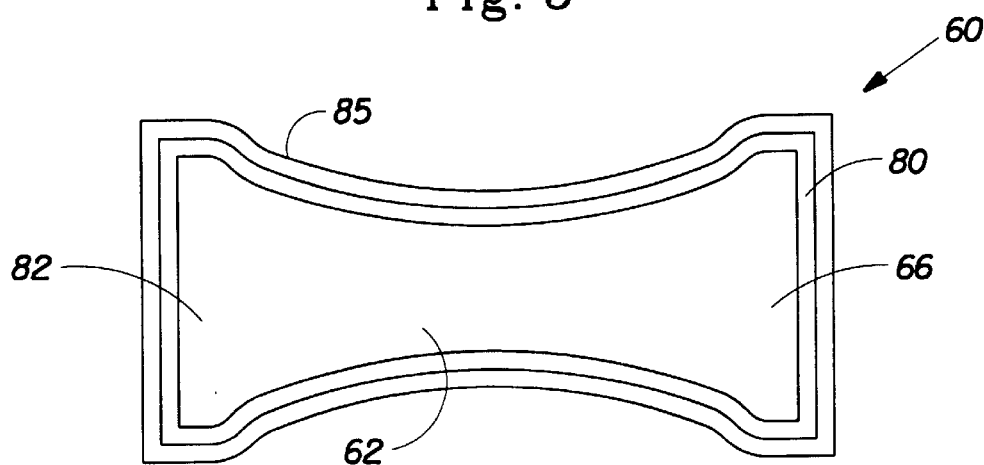
FIG. 6 is a plan view of an alternative embodiment of the present invention.

In addition to the barrier material(s) 68, the waste passage member 60 may include one or more body adhering compositions 80 which act to hold the waste passage member 60 close to the wearer's skin. Such body adhering compositions 80 may be integral with the material making up the waste passage member 60 or may be separate materials disposed directly or indirectly on all or any portion of the waste passage member 60. In one preferred embodiment, as shown in FIG. 6, the body adhering composition 80 is disposed on a portion of the body facing surface 62 of the waste passage member 60. In especially preferred embodiments, the body adhering composition 80 is disposed adjacent at least a portion of the peripheral edge 85 of the waste passage member 60. However, embodiments are contemplated wherein the body adhering composition 80 is located away from the peripheral edges 85. The body adhering composition 80 may be disposed on the waste passage member 60 in any pattern or configuration including, but not limited to lines, stripes, dots, and the like.

The body adhering composition 80 can include any one or more substances capable of releasably adhering to the skin of the wearer. Further, the body adhering composition 80 may be in the form of a gel, lotion, film, web or the like. Examples of suitable body adhering compositions include adhesives, gelatin, petrolatum waxes such as silicone or petroleum waxes, oils such as silicone or petroleum based oils, skin care compositions or ingredients thereof, as described below, and the like. Suitable adhesives include, but are not limited to, hydrogel or hydrocolloid adhesives such as acrylic based polymeric adhesives, and the like. (Some exemplary hydrogel and/or hydrocolloid adhesives are disclosed in U.S. Pat. Nos. 4,231,369; 4,593,053; 4,699, 146; 4,738,257; and 5,726,250; each of which is incorporated by reference herein.) The adhesives may also include any "medical adhesive" which is compatible for use with biological tissue, such as skin. Acrylic medical adhesives suitable for use as body adhering compositions 80, include adhesives available from Adhesive Research, Inc., of Glen Rock, Pa., under the designations MA-46, MA-312, "MTTM" High MVTR adhesive, and AS-17. Rubber-bases medical adhesives, such as SB-2 from Adhesive Research Inc. may also be suitable. Other exemplary adhesives include Dow Corning Medical Adhesive (Type B) available from Dow Corning, Midland, Mich.; "MEDICAL ADHESIVE" from Hollister Inc., of Libertyville, Ill.; 3M Spray Adhesives #79, 76, 77 and 90 available from the 3M Corp. of St. Paul, Minn.; and "MATISOL" liquid adhesive available from Ferndale Laboratories of Ferndale, Mich. Other medical adhesives are described in U.S. Pat. Nos. 4,078,568; 4,140,115; 4,192,785; 4,393,080; 4,505,976; 4,551,490; 4,768,503 and polyacrylate and polymethacrylate hydrogel adhesives are disclosed in U.S. Pat. Nos. 5,614,586 and 5,674,275; the disclosure of each of which is incorporated by reference herein. Yet another exemplary adhesive comprising polyvinyl pyrollidone and a multi-functional amine-containing polymer is disclosed in WO 94/13235A1. (The disclosure of each of these references is incorporated herein by reference.) Alternative body adhering means which may be used in place of or in addition to those described above include static electricity, suction and the like. In any case, it is preferred that the body adhering composition 80 permit vapors to pass (i.e., breathable), be compatible with the skin and otherwise skin friendly.

In preferred embodiments as described in co-pending EPO Application nos. 97110730.5 and 97120336.9 (both of which are incorporated by reference herein), removal of the body adhering composition from the skin is relatively painless. In these embodiments, the body adhesive or body adhering composition has an elastic modulus at a temperature of 37° C. (100° Fahrenheit) abbreviated $G'_{37}$ and a viscous modulus at a temperature of 37° C. (100° Fahrenheit) of $G''_{37}$. The adhesive further has a dynamic elastic behavior defined as $\Delta G'_{37}$ which is the difference of $G'_{37}$ at a frequency of 100 rad/sec and $G'_{37}$ at a frequency of 1 rad/sec and a dynamic viscous behavior $\Delta G''_{37}$ which is the difference of $G''_{37}$ at a frequency of 100 rad/sec and $G''_{37}$ at a frequency of 1 rad/sec. Further, the body adhesive preferably satisfies the following conditions.

$G'_{37}$ (1 rad/sec) is in the range of about 1500 Pa to about 20000 Pa, preferably of about 1500 Pa to about 15000 Pa, most preferably of about 3000 Pa to of about 10000 Pa.

$G''_{37}$ (1 rad/sec) is in the range of about 100 Pa to about 15000 Pa, preferably of about 100 Pa to of about 10000 Pa, most preferably 300 Pa to of about 5000 Pa.

The ratio of $G'_{37}$ (1 rad/sec)/$G''_{37}$ (1 rad/sec) is in the range of about 3 to about 30.

The ratio $G'_{37}$ (100 rad/sec)–$G'_{37}$ (100 rad/sec)/$G'_{37}$ (1 rad/sec)–$G''_{37}$ (1 rad/sec) is not less than about 0.5, preferably in the range of about 0.7 to 3, most preferably in the range of about 1 to about 1.8.

Either the ratio of $\Delta G'_{37}/G'_{37}$ (1 rad/sec) is not greater than about 1.5, preferably not greater than about 0.8, or $\Delta G'_{37}$ is not greater than about 10000 Pa, preferably less than 5000 Pa, most preferably less than about 2000 Pa, or both.

The value of the ratio $G'_{37}/G''_{37}$ at least for the frequency range from about 1 rad/s up to 100 rad/s should preferably about 3.3 or above, more preferably about 5 or above, most preferably about 10 or above while not exceeding about 50, preferably about 30, anywhere in the frequency interval.

To obtain the desired characteristics, the body adhering composition may comprise: from 0.5 to 20%, preferably 5% to 15%, by weight of a macromolecular polymeric substance or a mixture of such substances soluble or swellable in the below mentioned plasticizer(s). As not limiting examples such macromolecular or polymeric substances can be natural and/or synthetic such as natural gums or derivatives such as natural gums and gelatins, their derivatives and alginates; polyacrylics; polyvinyl alcohol; polyethylene oxide; poly-vinylpyrrolidon (PVP) or polyvinylethers, their copolymers and derivatives; cellulose derivatives; Block Copolymer Thermoplastic Elastomers and preferably Styrenic block Copolymers and more preferably the hydrogenated grades Styrol/Ethylene-Butylene/Styrol (SEBS), Styrene/Isoprene/Styrene (SIS), and Styrol/Ethylene-Propylene/Styrol (SEPS). Further, preferred body adhesive compositions may comprise from 45 to 99.5% by weight, preferably from 51 to 99.5% by weight, of a plasticizing substance or a mixture of plasticizing substances, which are liquid at room temperature. As non-limiting examples the plasticizer can be water, various alcohols (like in particular glycerol), gylcols and their ethers, polyglycols, liquid polybutenes, esters such phtalates, adipates, stearates, palmitates, sebacates, or myristates, natural or synthetic oils such as vegetable oils, mineral oils, or combinations thereof Further, the body adhesive may include from 0% to 50% by weight of the composition, preferably 0% to 600% by weight of the macromolecular polymeric substance, of a tackifying resin whose main scope is to tailor the Tg especially in systems based on synthetic polymers. Also, preferred body adhesives may include from 0 to 10% and more preferably from 0 to 5% by weight of substances for facilitating and stabilizing the gel and the gel forming. process both of hydrophilic or hydrophobic liquid plasticizers. These may be for oily systems, e.g., the fatty acids of $C_8$ to $C_{22}$, their metallic salts and their polyoxo-derivatives; lanolin derivatives; silica; bentonite, montmorillonite and their derivatives; polyamides, waxes or mixtures thereof.

Common additives known in the art as preservative, antioxidants, anti UV, pigments, mineral fillers, rheology modifiers and the like can also be comprised in quantities up to 10% each. Also, when chemical crosslinks are formed in the system, a cross-linking agent can be present preferably in quantities up to 5% by weight. Chemical crosslinking can be formed also by mutual neutralization of polymers having different functionalities as in the reaction between acid polyacrylics and polysaccharides.

Suitable skin care compositions which may be used as, with, or in place of the body adhering compositions include Category I actives as defined by the U.S. Federal Food and Drug Administration's (FDA) Tentative Final Monograph on Skin Protectant Drug Products for Over-the-Counter Human Use, which presently include: alantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Federal Food and Drug Administration's Tentative Final Monograph on Skin Protectant Drug Products for Over-the-Counter Human Use tentative final monograph on skin protectant drug products for over-the-counter human use, which presently include: live yeast cell derivatives, aldioxa, aluminum acetate, microporous cellulose, cholecalciferol, colloidal oatmeal, cysteine hydrochloride, dexpanthanol, Peruvian balsam oil, protein hydrolysates, racemethionine, sodium bicarbonate, Vitamin A, and the like. Many of the FDA monographed skin care ingredients are currently utilized in commercially available skin care products, such as "A AND D" Ointment, "VASELINE" Petroleum Jelly, "DESITIN" Diaper Rash Ointment and Daily Care Ointment, "GOLD BOND" Medicated Baby Powder, "AQUAPHOR" Healing Ointment, "BABY MAGIC" Baby Lotion, "JOHNSON'S ULTRA SENSITIVE" Baby Cream, Johnson's baby lotion, lip balms, etc. Other suitable skin care compositions (e.g., lotions) are described in detail in U.S. Pat. Nos. 5,643,588; 5,607,760; 5,609,587; and 5,635,191; each of these references being incorporated herein by reference.

The skin care compositions may also include (feces chemical modification agents), pH control agents, enzyme inhibitors, antimicrobials, odor absorbing agents (such as cyclodextrins or activated charcoal), or antimicrobials. Examples of enzyme inhibitors include protease inhibitors (e.g., hexamidine derivatives), lipase inhibitors (e.g., triacetin), urease inhibitors, and the like. Citric acid is an example of a suitable proton-donating pH control agent. In one preferred embodiment, a skin care composition comprising about 57% by wt. petrolatum, about 42% by wt. stearyl alcohol, and about 1% aloe extract is applied to the outer 1 cm of the waste passage member 60 at add-on level of about 5 mg/cm$^2$.

Figure 2:
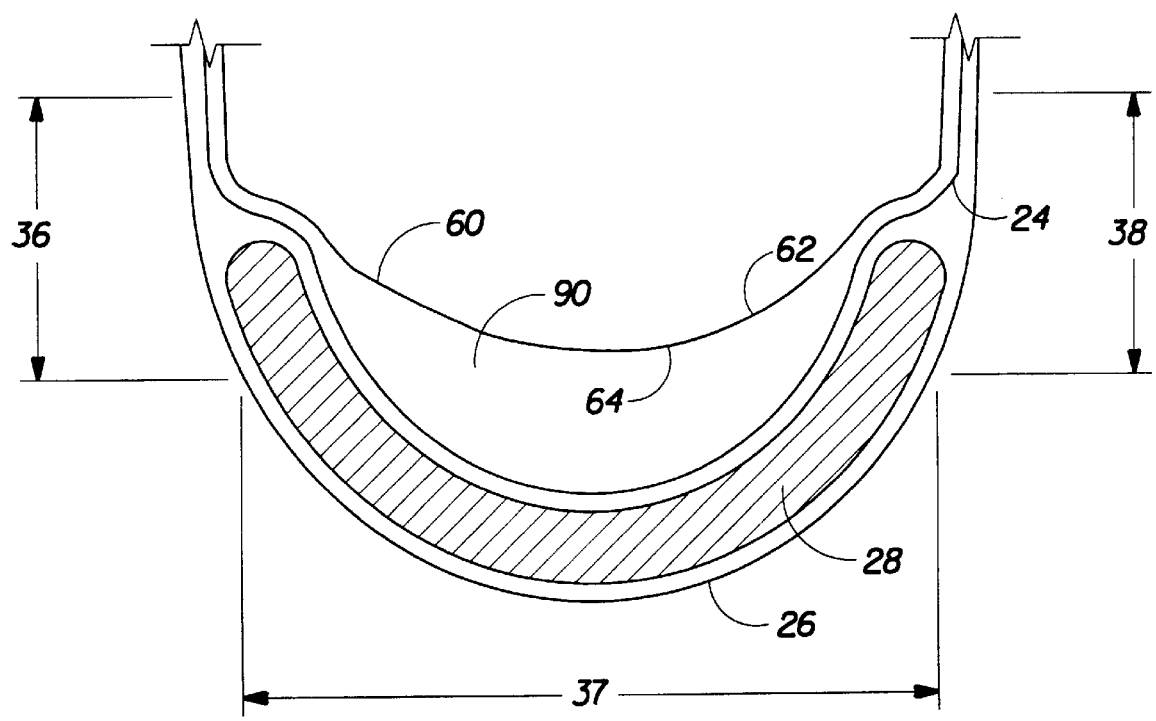
FIG. 2 is a cross-sectional view of one embodiment of the present invention shown as it would be configured on a wearer.

FIGS. 1 and 2 show one preferred embodiment of the present invention wherein the waste passage member 60 is permanently joined to an absorbent article, such as a diaper 20. Although the waste passage member 60 can be located anywhere in or on the diaper 20, it is preferably located such that at least a portion of the waste passage member 60 is disposed in the crotch region 37. It is also preferred that the waste passage member 60 be disposed such that at least a portion of the waste passage member 60 will be in intimate contact with the wearer's skin during use. Accordingly, the waste passage member 60 may be located adjacent the body facing surface 47 of the core 28. If the diaper 20 includes a topsheet 24, the waste passage member 60 is preferably located on top of, or outwardly from, the topsheet 24 and toward the wearer's body. This configuration will ensure that the topsheet 24 does not interfere with the movement of the bodily waste through the waste passage member 60. Alternatively, the waste passage member 60 may be disposed below the topsheet 24 or between the topsheet and the core 28 or other underlying structure. In other embodiments, the waste passage member 60 may be an integral part of the topsheet 24 or any other part of the diaper, such as cuffs, a transverse barrier, a pocket feature or the like. In any case, it may be preferable to configure the waste passage member 60 such that it is separated from the underlying structure of the diaper 20 by a void and/or spacing element or member. A void 90, such as the one shown in FIG. 2, may increase the efficacy of the waste passage member 60, and thus the diaper 20, by providing a location where the waste can be stored and/or immobilized away from the wearer's skin. The void 90 may be created by any known element or means including elastics or shrink members which foreshorten the waste passage member 60, or spacing members (including those mentioned above) which provide a structure which physically separates portions of the diaper 20. It may also be desirable to leave at least a portion of the waste passage member 60 free from attachment to the underlying structure of the diaper 20 in at least a portion of the crotch region 37.

As noted above, the waste passage member 60 may be disposed anywhere in the diaper 20 and may be integral with or joined to any portion thereof, such as the topsheet 24. In one preferred embodiment, as shown in FIG. 1, the waste passage member 60 is a separate element from the topsheet 24 and is disposed outwardly from the topsheet 24, toward the wearer's skin during use. The waste passage member 60 extends from the first waist region 36, through the crotch region 37 to the second waist region 38. Preferably, the waste passage member 60 is joined about its peripheral edges 85, most preferably in at least one of the waist regions. As shown in FIG. 2, the waste passage member 60 may be joined to the underlying structure of the diaper 20 in both the first waist region 36 and second waist region 38. In other embodiments, waste passage member 60 may make up, be joined to, or be integral with one or more barrier leg cuffs, a transverse barrier, waste pockets or any other element or structure of the diaper 20. In any case, it is preferred that the waste passage member 60 be disposed such that at least a portion of the member is located adjacent the wearer's anus, urethra, and/or vagina while the diaper is being worn.

If the waste passage member 60 is joined to any part of the diaper 20, it may be joined to the underlying structure of the diaper continuously or intermittently. Further, the waste passage member 60 may be joined permanently or may be releasably or refastenably joined to the diaper 20. Suitable permanent joining means include, but are not limited to adhesive, heat, pressure, laser, sonic, electromagnetic bonding, combinations thereof or any other known bonding means. Suitable releasable and refastenable joining means include, but are not limited to hook and loop fasteners, adhesives, snaps, clips, magnetic bonds, electrostatic bonds and the like.

The waste passage member 60 may also comprise one or more apertures, slits, slots, perforations and/or weakened regions to aid penetration by the waste material. Further, the rate of dissolution of the soluble material 66 may be enhanced by reducing the strength or thickness of the soluble material 66 or increasing its effective surface area (i.e., by roughening, scoring, perforating, or slitting it). Other known mechanical and/or chemical modifications may be made to the waste passage member 60 to provide any other desired properties, including but not limited to strength, breathability, adhesion, penetration, feel and aesthetics.

It may also be desirable to provide some or all of the waste passage member 60 with elasticity or extension characteristics. For example, portions of the waste passage member 60 may include elastics which gather (foreshorten) the waste passage member 60 and pull it close to the wearer's skin during use. The elastic material may provide elasticity at all times or only before of after certain mechanical or chemical inputs. For example, the waste passage member 60 may include heat shrinkable water activated elastic elements which gather the waste passage member 60 after being subjected to heat or water, respectively. Thus, embodiments are contemplated wherein the waste passage member 60 lies flat along the topsheet 24, if present, core 28 or other underlying structure until worn or until the wearer excretes bodily waste which activates the elastomer and foreshortens the waste passage member 60. Alternatively, the waste passage member 60 itself may include an elastomeric or extensible material or may be processed to provide elastic like stretch characteristics. Suitable means for providing elastic-like stretch characteristics to nonelastic materials are described in above-mentioned U.S. Pat. No. 5,518,801, which is incorporated by reference herein.

Figure 3:
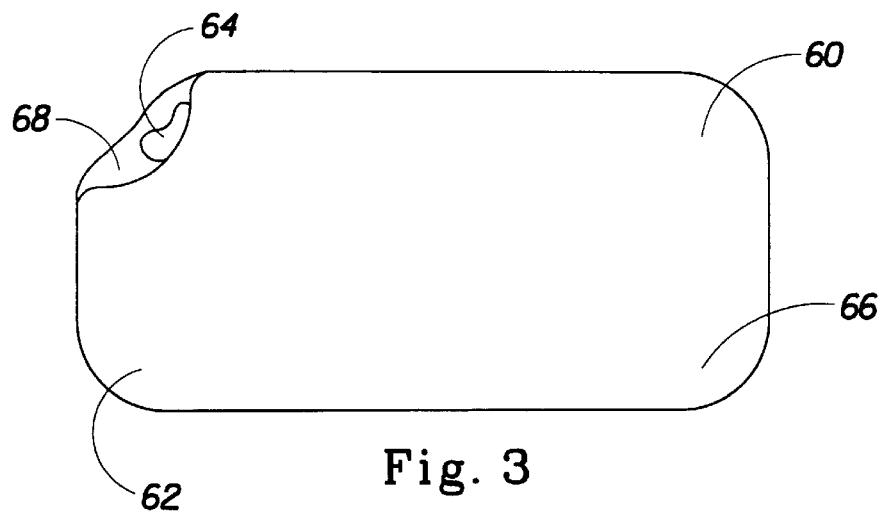
FIG. 3 is a plan view of one embodiment of the directionally preferential waste passage member of the present invention.
Figure 4:
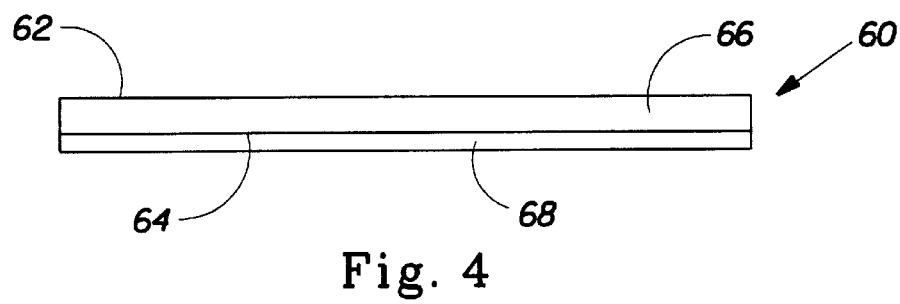
FIG. 4 is a cross-section view of the directionally preferential waste passage member shown in FIG. 2.

In an alternative embodiment to the disposable absorbent article described herein, the waste passage member 60 may be a separate structure which can be used with or independent from a containment article such as a diaper, adult incontinence device, sanitary napkin, diaper cover or the like. As shown in FIGS. 3 and 4, the waste passage member 60 may comprise a single material having a body surface 62 and a garment surface 64. As described above, at least a portion of the body surface 62 preferably includes a bodily waste soluble material 66. That is, at least a portion of the body surface 62 will dissolve when contacted by certain bodily waste so as to permit the waste to pass through the waste passage member 60 away from the wearer's skin. As with the embodiments described above, at least a portion of the garment surface 64 includes a barrier material 68 which resists or prevents the movement of the waste back through the waste passage member 60 toward the wearer's skin.

If not integrated into an article such as a diaper, it is important for the waste passage member 60 to have some means by which to maintain itself in close proximity to the wearer's body. Although belts, straps or other known means can be used, it is preferred that the waste passage member 60 include a body adhering composition 80, as described above. The body adhering composition 80 nay be disposed anywhere on the waste passage member 60. In preferred embodiments, the body adhering composition 80 is selectively disposed on the body surface 62 so as to permit the waste passage member 60 to be securely adhered to the body in the desired location (e.g. about the anus and/or urethra) without substantially hindering the solubility of the soluble material 66.

The waste passage member 60 may be any shape and/or size. In preferred embodiments, as shown in FIGS. 3 and 6, the waste passage member 60 may be generally rectangular or generally hour glass shaped. However, other shapes are contemplated including, but not limited to, circles, ovals, squares, triangles and the like. Other more complex shapes are also envisioned which permit the waste passage member 60 to fit closely to different parts of the body, such as the anus, urethra or vagina. In one preferred embodiment, the waste passage member 60 is rectangular and has dimensions of about 10 cm×about 30 cm.

The waste passage member 60 may also include other shaping or fit features such as elastics, slits, three dimensional shaping, and the like. Further, the waste passage member 60 may include fasteners to join the waste passage member 60 to articles such as diapers, incontinence garments, underwear and the like. Such fasteners may include, but are not limited to buttons, zippers, tapes, hook and loop fasteners, snaps, buckles and the like.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An article for preventing bodily exudates from contacting a wearer's skin, the article comprising:

a directionally preferential waste passage member having a body facing surface and an opposed garment facing surface, at least a portion of the body facing surface of the directionally preferential waste passage member including an enzyme degradable material which degrades when contacted by enzymes found in bodily exudates so at to permit the bodily exudates to pass through the directionally preferential waste passage member in a first direction generally away from the wearer's skin, and at least a portion of the garment facing surface of the directionally preferential waste passage member including a barrier material which resists penetration by the bodily exudates in second direction generally opposite to the first direction.

2. The absorbent article of claim 1 wherein the barrier material is selected from the group consisting of: silicones, oils, waxes, and polytetrafluoroethylene based compositions.

3. The article of claim 1 further comprising a body adhering composition disposed on or integral with the body facing surface of the directionally preferential waste passage member.

4. The article of claim 3 wherein the body adhering composition is selected from the group consisting of: gelatins, silicones, oils, waxes, hydrocolloid and hydrogel adhesives.

5. The article of claim 1 wherein the enzyme degradable material is located such that it is adjacent the wearer's anus or urethra when worn.

6. The article of claim 1 wherein the directionally preferential waste passage member includes a reticulated insoluble member having interstices, at least some of the interstices having the enzyme degradable material disposed therein.

* * * * *